United States Patent
Bolotin et al.

(10) Patent No.: US 8,628,976 B2
(45) Date of Patent: Jan. 14, 2014

(54) METHOD FOR THE DETECTION OF BIOLOGIC PARTICLE CONTAMINATION

(75) Inventors: Charles E. Bolotin, Oro Valley, AZ (US); Martin Van Trieste, Thousand Oaks, CA (US)

(73) Assignee: Azbil Biovigilant, Inc., Tucson, AZ (US)

( * ) Notice: Subject to any disclaimer, the term of this patent is extended or adjusted under 35 U.S.C. 154(b) by 809 days.

(21) Appl. No.: 12/327,674

(22) Filed: Dec. 3, 2008

(65) Prior Publication Data

US 2009/0242799 A1     Oct. 1, 2009

Related U.S. Application Data

(60) Provisional application No. 61/005,305, filed on Dec. 3, 2007.

(51) Int. Cl.
     *G01N 21/76*      (2006.01)

(52) U.S. Cl.
     USPC .......................... 436/172; 436/104; 436/181

(58) Field of Classification Search
     USPC ......................................... 436/172, 104, 181
     See application file for complete search history.

(56) References Cited

U.S. PATENT DOCUMENTS

| | | | |
|---|---|---|---|
| 2,675,697 A | 4/1954 | Quynn et al. | |
| 3,457,407 A | 7/1969 | Goldberg | 250/373 |
| 3,540,261 A | 11/1970 | Scoggins | |
| 3,710,933 A | 1/1973 | Fulwyler et al. | 209/3.1 |
| 3,715,911 A | 2/1973 | Chuan | |
| 3,826,364 A | 7/1974 | Bonner et al. | 209/3.1 |
| 3,845,480 A | 10/1974 | Steinberg | |
| 3,850,525 A | 11/1974 | Kaye | 356/73 |
| 3,867,640 A | 2/1975 | Paulsen | |
| 4,046,593 A | 9/1977 | Au et al. | |
| 4,080,832 A | 3/1978 | Moody et al. | |
| 4,091,674 A | 5/1978 | Amey | |
| 4,117,715 A | 10/1978 | Hoenig | |
| 4,175,865 A | 11/1979 | Horvath et al. | |
| 4,226,533 A | 10/1980 | Snowman | |
| 4,245,910 A | 1/1981 | Kallander | |
| 4,249,244 A | 2/1981 | Shofner et al. | |
| 4,251,733 A | 2/1981 | Hirleman, Jr. | 356/335 |

(Continued)

FOREIGN PATENT DOCUMENTS

| | | | |
|---|---|---|---|
| DE | 2 401 008 | 8/1974 | |
| EP | 0435166 | 7/1991 | G01N 15/14 |

(Continued)

OTHER PUBLICATIONS

"Continuous, Rapid Biological Aerosol Detection with the Use of Fluorescence: Outdoor Test Results" Eversole et al., Field Analytical Chemistry and Technology 3(4-5):249-259,1999.

(Continued)

*Primary Examiner* — Monique Cole

(74) *Attorney, Agent, or Firm* — Michael J. Curley; Dale F. Regelman; Quarles & Brady LLP

(57) ABSTRACT

Methods for detecting particles in a fluid, including determining particle size and intrinsic fluorescence of a particle, and time correlating the particle detection data with image data in the vicinity of the detector or detector inlet to identify contamination sources in clean environments are described.

15 Claims, 3 Drawing Sheets

(56) References Cited

U.S. PATENT DOCUMENTS

| | | | |
|---|---|---|---|
| 4,254,414 A | 3/1981 | Street et al. | |
| 4,255,014 A | 3/1981 | Ellis | 359/371 |
| 4,286,876 A | 9/1981 | Hogg et al. | |
| 4,348,111 A | 9/1982 | Goulas et al. | 356/336 |
| 4,350,507 A | 9/1982 | Greenough et al. | |
| 4,355,897 A | 10/1982 | Kaye | 356/338 |
| 4,375,667 A | 3/1983 | Buchan | |
| 4,389,903 A | 6/1983 | Bertone et al. | |
| 4,420,256 A | 12/1983 | Fladda et al. | |
| 4,475,379 A | 10/1984 | Jinotti | |
| 4,569,235 A | 2/1986 | Conkle et al. | |
| 4,575,181 A | 3/1986 | Ishikawa | |
| 4,583,859 A | 4/1986 | Hall, II | |
| 4,599,307 A | 7/1986 | Saunders et al. | 435/34 |
| 4,617,560 A | 10/1986 | Gutmann | |
| 4,727,020 A | 2/1988 | Recktenwald | 435/6 |
| 4,728,190 A | 3/1988 | Knollenberg | |
| 4,737,648 A | 4/1988 | Smith et al. | |
| 4,786,295 A | 11/1988 | Newman et al. | |
| 4,786,472 A | 11/1988 | McConnell et al. | |
| 4,830,494 A | 5/1989 | Ishikawa et al. | |
| 4,839,463 A | 6/1989 | Kumaki | |
| 4,839,529 A | 6/1989 | Fruengel | |
| 4,851,817 A | 7/1989 | Brossia et al. | |
| 4,940,326 A | 7/1990 | Tatsuno | 356/336 |
| 4,994,682 A | 2/1991 | Woodside | |
| 5,001,463 A | 3/1991 | Hamburger | |
| 5,005,005 A | 4/1991 | Brossia et al. | |
| 5,006,986 A | 4/1991 | Inoue | |
| 5,056,918 A | 10/1991 | Bott et al. | 356/336 |
| 5,083,865 A | 1/1992 | Kinney et al. | |
| 5,085,500 A | 2/1992 | Blesener | |
| 5,101,113 A | 3/1992 | Hirleman, Jr. et al. | |
| 5,117,357 A | 5/1992 | Inoue | |
| 5,121,988 A | 6/1992 | Blesener et al. | |
| 5,123,731 A | 6/1992 | Yoshinaga et al. | |
| 5,125,737 A | 6/1992 | Rodriguez et al. | |
| 5,132,548 A | 7/1992 | Borden et al. | |
| 5,166,537 A | 11/1992 | Horiuchi et al. | |
| 5,180,065 A | 1/1993 | Touge et al. | |
| 5,231,378 A | 7/1993 | Dennis et al. | |
| 5,257,087 A | 10/1993 | Furuya | 356/336 |
| 5,266,798 A | 11/1993 | Borden et al. | |
| 5,286,452 A | 2/1994 | Hansen | |
| 5,305,072 A | 4/1994 | Sawada et al. | |
| 5,315,115 A | 5/1994 | Gerber | |
| 5,366,858 A | 11/1994 | Koizumi et al. | |
| 5,383,024 A | 1/1995 | Maxey et al. | |
| 5,408,307 A | 4/1995 | Yamamoto et al. | 356/73 |
| 5,416,580 A | 5/1995 | Trainer | |
| 5,420,717 A | 5/1995 | Tabata | 359/371 |
| 5,426,501 A | 6/1995 | Hokanson et al. | |
| 5,428,964 A | 7/1995 | Lobdell | |
| 5,448,364 A | 9/1995 | Moran | |
| 5,456,102 A | 10/1995 | Moorehead | |
| 5,457,526 A | 10/1995 | Kosaka | |
| 5,467,189 A | 11/1995 | Kreikebaum et al. | 356/336 |
| 5,469,251 A | 11/1995 | Kosaka et al. | 356/73 |
| 5,481,357 A | 1/1996 | Ahsan et al. | |
| 5,506,673 A | 4/1996 | Kosaka et al. | |
| 5,540,494 A | 7/1996 | Purvis, Jr. et al. | |
| 5,561,515 A | 10/1996 | Hairston et al. | |
| 5,600,438 A | 2/1997 | Kreikebaum et al. | |
| 5,646,597 A | 7/1997 | Hamburger et al. | 340/627 |
| 5,684,585 A | 11/1997 | Girvin | |
| 5,695,583 A | 12/1997 | Van Den Bergh et al. | |
| 5,701,012 A | 12/1997 | Ho | |
| 5,760,900 A | 6/1998 | Ito et al. | 356/338 |
| 5,864,399 A | 1/1999 | Girvin et al. | |
| 5,889,276 A | 3/1999 | Yonezawa et al. | 250/201.3 |
| 5,895,922 A | 4/1999 | Ho | |
| 5,946,093 A | 8/1999 | DeFreez et al. | |
| 5,966,204 A | 10/1999 | Abe | 356/51 |
| 5,969,622 A | 10/1999 | Hamburger et al. | |
| 5,986,555 A | 11/1999 | Hamburger et al. | |
| 5,995,686 A | 11/1999 | Hamburger et al. | |
| 5,999,250 A | 12/1999 | Hairston et al. | |
| 6,008,729 A | 12/1999 | Hamburger et al. | |
| 6,025,956 A | 2/2000 | Nagano et al. | 359/386 |
| 6,087,947 A | 7/2000 | Hamburger et al. | 340/627 |
| 6,312,914 B1 | 11/2001 | Kardos et al. | 435/6 |
| 6,386,015 B1 | 5/2002 | Rader et al. | 73/31 |
| 6,537,829 B1 | 3/2003 | Zarling et al. | 436/514 |
| 6,600,598 B1 | 7/2003 | Piekos | 359/385 |
| 6,643,061 B2 | 11/2003 | Osa et al. | 359/385 |
| 6,819,411 B1 | 11/2004 | Sharpe et al. | 356/72 |
| 6,831,279 B2 | 12/2004 | Ho | |
| 6,885,440 B2 | 4/2005 | Silcott et al. | |
| 6,891,671 B1 | 5/2005 | Greenberg | 359/388 |
| 6,924,893 B2 | 8/2005 | Oldenbourg et al. | 356/369 |
| 6,972,424 B1 | 12/2005 | Quist et al. | 250/573 |
| 7,053,783 B2 | 5/2006 | Hamburger et al. | |
| 7,106,442 B2 | 9/2006 | Silcott et al. | 356/338 |
| 7,319,039 B2* | 1/2008 | Sullivan | 436/172 |
| 7,430,046 B2 | 9/2008 | Jiang et al. | 356/336 |
| 2001/0012429 A1 | 8/2001 | Wach et al. | 385/115 |
| 2001/0024800 A1 | 9/2001 | Garcia-Rubio et al. | 435/7.21 |
| 2002/0028519 A1 | 3/2002 | Yguerabide et al. | 436/518 |
| 2002/0032165 A1 | 3/2002 | Johnson et al. | 514/44 |
| 2002/0045190 A1 | 4/2002 | Wilson, Jr. et al. | |
| 2002/0045276 A1 | 4/2002 | Yguerabide et al. | 436/518 |
| 2002/0046966 A1 | 4/2002 | Muscate-Magnussen | 210/198.2 |
| 2002/0065468 A1 | 5/2002 | Utzinger et al. | 600/476 |
| 2002/0103517 A1 | 8/2002 | West et al. | 607/88 |
| 2002/0119486 A1 | 8/2002 | Oberhardt | 435/6 |
| 2002/0132766 A1 | 9/2002 | DeGrado et al. | 514/12 |
| 2002/0135752 A1 | 9/2002 | Sokolov et al. | 356/39 |
| 2002/0143243 A1 | 10/2002 | Georgakoudi et al. | 600/310 |
| 2002/0165456 A1 | 11/2002 | Canpolat et al. | 600/473 |
| 2002/0171831 A1 | 11/2002 | Backman et al. | 356/369 |
| 2003/0013973 A1 | 1/2003 | Georgakoudi et al. | 600/473 |
| 2003/0022249 A1 | 1/2003 | Schmitz et al. | 435/7.21 |
| 2003/0030783 A1 | 2/2003 | Roche et al. | 356/39 |
| 2003/0052281 A1 | 3/2003 | Rader et al. | 250/461.1 |
| 2003/0077627 A1 | 4/2003 | Worthington et al. | 435/6 |
| 2003/0093092 A1 | 5/2003 | West et al. | 606/139 |
| 2003/0096302 A1 | 5/2003 | Yguerabide et al. | 435/7.1 |
| 2003/0098421 A1 | 5/2003 | Ho | 250/458.1 |
| 2003/0098422 A1* | 5/2003 | Silcott et al. | 250/458.1 |
| 2003/0124733 A1 | 7/2003 | Bushway et al. | 436/174 |
| 2003/0137669 A1 | 7/2003 | Rollins et al. | 356/479 |
| 2003/0139886 A1 | 7/2003 | Bodzin et al. | 702/28 |
| 2003/0157731 A1 | 8/2003 | Yguerabide et al. | 436/523 |
| 2003/0157732 A1 | 8/2003 | Baker et al. | 436/531 |
| 2003/0159498 A1 | 8/2003 | Small | 73/24.02 |
| 2003/0207328 A1 | 11/2003 | Yguerabide et al. | 435/7.1 |
| 2003/0223063 A1* | 12/2003 | Hill et al. | 356/340 |
| 2003/0228682 A1 | 12/2003 | Lakowicz et al. | 435/287.2 |
| 2003/0231309 A1 | 12/2003 | Fulghum, Jr. et al. | 356/338 |
| 2003/0232445 A1 | 12/2003 | Fulghum, Jr. | 436/63 |
| 2003/0235919 A1 | 12/2003 | Chandler | |
| 2004/0009941 A1 | 1/2004 | Johnson et al. | 514/44 |
| 2004/0011975 A1 | 1/2004 | Nicoli et al. | 250/574 |
| 2004/0021861 A1 | 2/2004 | Lewis et al. | 356/326 |
| 2004/0023317 A1 | 2/2004 | Motamedi et al. | 435/14 |
| 2004/0038413 A1 | 2/2004 | Kramer | 436/63 |
| 2004/0057050 A1 | 3/2004 | Beck et al. | 356/336 |
| 2004/0072356 A1 | 4/2004 | Senisterra et al. | 436/63 |
| 2004/0073120 A1 | 4/2004 | Motz et al. | 600/478 |
| 2004/0079893 A1 | 4/2004 | Dietz et al. | 250/458.1 |
| 2004/0159799 A1 | 8/2004 | Saccomanno | 250/461.1 |
| 2004/0161143 A1 | 8/2004 | Dietz et al. | 382/133 |
| 2004/0174821 A1 | 9/2004 | Eggeling et al. | 370/252 |
| 2004/0197232 A1 | 10/2004 | Kramer | 422/73 |
| 2004/0218184 A1 | 11/2004 | Jorgenson et al. | 356/419 |
| 2005/0019842 A1 | 1/2005 | Prober et al. | 435/7.9 |
| 2005/0020922 A1 | 1/2005 | Frangioni et al. | 600/473 |
| 2005/0020923 A1 | 1/2005 | Frangioni et al. | 600/473 |
| 2005/0026831 A1 | 2/2005 | Bodmer et al. | 514/12 |
| 2005/0057749 A1 | 3/2005 | Dietz et al. | 356/318 |
| 2005/0073683 A1* | 4/2005 | Gard et al. | 356/337 |
| 2005/0079526 A1 | 4/2005 | Senisterra et al. | 435/6 |
| 2005/0105077 A1 | 5/2005 | Padmanabhan et al. | 356/39 |
| 2005/0112784 A1 | 5/2005 | Yguerabide et al. | 436/518 |

(56) References Cited

U.S. PATENT DOCUMENTS

| | | | |
|---|---|---|---|
| 2005/0119541 A1 | 6/2005 | Lorenz et al. | 600/316 |
| 2005/0130324 A1 | 6/2005 | West et al. | 436/523 |
| 2005/0137130 A1 | 6/2005 | Bodmer et al. | 514/12 |
| 2005/0141843 A1 | 6/2005 | Warden et al. | 385/141 |
| 2005/0147533 A1 | 7/2005 | Cole et al. | 422/73 |
| 2005/0172852 A1 | 8/2005 | Anderson et al. | 106/31.03 |
| 2005/0194546 A1 | 9/2005 | Saccomanno | 250/461.1 |
| 2005/0220886 A1 | 10/2005 | Bodmer et al. | 424/489 |
| 2005/0240107 A1 | 10/2005 | Alfano et al. | 600/476 |
| 2005/0243307 A1* | 11/2005 | Silcott et al. | 356/73 |
| 2005/0243314 A1 | 11/2005 | Chinnock | 356/364 |
| 2006/0011776 A1* | 1/2006 | Maurer et al. | 244/1 R |
| 2006/0071075 A1 | 4/2006 | Moon et al. | |
| 2009/0095054 A1* | 4/2009 | Groves | 73/31.01 |
| 2012/0120385 A1* | 5/2012 | Jiang | 356/51 |

FOREIGN PATENT DOCUMENTS

| | | | |
|---|---|---|---|
| EP | 0463795 | 1/1992 | G08B 17/107 |
| EP | 0475748 | 3/1992 | G01N 21/88 |
| EP | 0595290 | 5/1994 | H02K 44/07 |
| EP | 0618440 | 10/1994 | G01N 21/53 |
| EP | 0711991 | 5/1996 | G01N 15/14 |
| EP | 0737307 | 10/1996 | G01N 15/14 |
| EP | 0214769 | 3/1997 | G01N 15/02 |
| EP | 1158292 A2 | 11/2001 | |
| GB | 1298658 | 12/1972 | |
| GB | 2044445 | 10/1980 | G01N 21/00 |
| GB | 2420616 | 5/2006 | |
| JP | 01247153 | 10/1989 | |
| JP | 02-165033 | 6/1990 | G01N 15/14 |
| JP | 03-108635 | 5/1991 | G01N 15/14 |
| JP | 04-185654 | 7/1992 | |
| JP | 8233728 | 9/1996 | |
| WO | WO 90/10282 | 9/1990 | |
| WO | 91/10123 | 7/1991 | |
| WO | 93/16368 | 8/1993 | |
| WO | 95/09354 | 4/1995 | |
| WO | WO 98/34094 | 8/1998 | G01N 15/02 |
| WO | WO 2007/011854 | 1/2007 | G08B 21/00 |

OTHER PUBLICATIONS

"Bio-Aerosol Fluorescence Sensor" Jeys et al., Proc. IRIS Active Systems, 1998, vol. 1, p. 235-249.

Casswell et al., Simslin II—A Portable Airborne Dust Measuring Instrument Employing a Light Scattering Technique, Conference Proceedings of the Fourth WVU Conference on Coal Mine Electrotechnology Article, Aug. 1978, 20-1-20-12.

Met One Model 228 and 229 Particle Concentration Meter and Particle Counter, Date Unknown, prior to 1996.

APC Airborne Particle Counter Model P3610 Article, Biotest, 2003.

Biotest Airborne Particle Monitor, Biotest Diagnostics Corp., "Microbial Air Samplers: RCS Plus and RCS Plus EX" 2003.

"Review Indentation Fracture: Principles and Applications" Lawn et al., Journal of Materials Science, 10, 1975, p. 1049-1081.

"Optimization of Electrolyte Material for use in Solid Oxide Electrolysis Cells" Brach, Thesis 2000, pp. 1-78.

"Near-Field Scanning Optical Microscopy" Dunn, Chem. Rev. 1999, 99, p. 2891-2927.

"Dynamic Vickers Indentation of Brittle Materials" Anton et al., Wear 239, 2000, p. 27-35.

"Direct Observation and Analysis of Indentation Cracking in Glasses and Ceramics" Cook et al., Journal Am. Ceram. Soc., 73, 1990, p. 787-817.

"Strength and Toughness of Tape-Cast Yttria-Stabilized Zirconia" Selcuk et al., Journal Am. Ceram. Soc., 83, 2000, p. 2029-2035.

"Experimental Method for a Dynamic Biaxial Flexural Strength of Test of Thin Ceramic Substrates" Cheng et al., Journal Am. Ceram. Soc., 85, 2002, p. 1203-1209.

"Evaluation of KIC of Brittle Solids by the Indentation Method with Low Crack-to-Indent Ratios" Niibara et al., Journal of Materials Science Letters 1, 1982, p. 13-16.

Inglesby et al., "Anthrax as a Biological Weapon", JAMA, May 12, 1999, vol. 281, No. 18, pp. 1735-1745 & published correction dated Apr. 19, 2000, vol. 283, No. 15, p. 1963.

Pan et al., "Backward-enhanced fluorescence from clusters of microspheres and particles of tryptophan", Applied Optics, vol. 41, No. 15, May 20, 2002, pp. 2994-2999.

Veselovskii et al., "Angle-and size-dependent characteristics of incoherent Raman and fluorescent scattering by microspheres", Applied Optics, Sep. 20, 2002, vol. 41, No. 27, pp. 5783-5791.

* cited by examiner

METHOD FOR THE DETECTION OF BIOLOGIC PARTICLE CONTAMINATION

CROSS REFERENCE TO RELATED APPLICATION

This application claims the benefit of U.S. Provisional Application Ser. No. 61/005,305, filed Dec. 3, 2007, the disclosure of which is hereby incorporated by reference.

FIELD OF THE INVENTION

The present invention relates generally to a system and methods for detecting airborne or liquidborne particles in an environment and for determining probable sources of the particles. More particularly the present invention relates to methods for detecting particles and distinguishing biologic particles from non-biologic particles, and to methods for identifying sources of the particulate contamination in the environment. The invention has particular utility in detecting particulate contamination and in determining the source of the particles, such as microbial particles (e.g. bacteria), in clean environments, and will be discussed in connection with such utility, although other utilities are contemplated.

BACKGROUND OF THE INVENTION

The monitoring for environmental contamination, including biological particles, is important in a number of industrial and commercial environments such as manufacturing facilities for pharmaceuticals, food and hospitals, and has also become important in public spaces such as airports, banks, postal handling facilities and government offices where there is concern for possible urban terrorist attacks.

In the pharmaceutical, healthcare and food industries a real time detector of environmental microbial levels is useful for public health, quality control and regulatory purposes. For example, parenteral drug manufacturers are required by the Food and Drug Administration to monitor the particulate and microbial levels in their aseptic clean rooms. Conventional microbiological methods require the collection of samples on growth media, and incubation at the correct temperature for the correct period of time (typically days). These methods assume that a viable microorganism is one that will undergo cellular division when placed in or on a growth media. For quantitative tests, growth is demonstrated by a visually detectable colony. There is a significant quantity of published literature that shows substantial limitations of using traditional culture and plate counting methods. For example, the published literature indicates variable results can be obtained depending upon the growth media used, the incubation time and temperature, and the condition of the microorganism prior to attempts to cultivate (e.g., slow growing, stressed, or sub-lethally damaged). Conventional methods also have no ability in real-time to locate probable sources of the contamination. In these applications, an instrument that can detect microbial particles, including bacteria, yeasts and molds, in the environment instantaneously and at low concentrations will be a useful tool and have significant advantages over conventional nutrient plate culture methods that require days for microbes to grow and be visually detected. It would also be useful to have an instrument that would be able to assist in locating, preferably in real-time, sources of particulate contamination.

There exist various prior art devices that employ particle size measurement and light induced fluorescence techniques as early warning sensors for bio-agents. Among these devices are fluorescence biological particle detection system of Ho (Jim Yew-Wah Ho, U.S. Pat. Nos. 5,701,012; 5,895,922; 6,831,279); FLAPS and UV-APS by TSI of Minnesota (Peter P. Hairston; and Frederick R. Quant; U.S. Pat. No. 5,999,250), and a fluorescence sensor by Silcott (U.S. Pat. No. 6,885,440). A proposed bio-sensor based on laser-induced fluorescence using a pulsed UV laser is described by T. H. Jeys, et al., Proc. IRIS Active Systems, vol. 1, p. 235, 1998. This is capable of detecting an aerosol concentration of five particles per liter of air, but involves expensive and delicate instruments. Other particle counters are manufactured by Met One Instrument, Inc. of Grants Pass, Oreg., Particle Measurement Systems, Inc., of Boulder, Colo., and Terra Universal Corp., of Anaheim, Calif.

Various detectors have been designed to detect airborne allergen particles and provide warning to sensitive individuals when the number of particles within an air sample exceeds a predetermined minimum value. Among these detectors are those described in U.S. Pat. Nos. 5,646,597, 5,969,622, 5,986,555, 6,008,729, 6,087,947, and 7,053,783, all to Hamburger et al. These detectors all involve direction of a light beam through a sample of environmental air such that part of the beam will be scattered by any particles in the air, a beam blocking device for transmitting only light scattered in a predetermined angular range corresponding to the predetermined allergen size range, and a detector for detecting the transmitted light.

Improved methods for the detection of airborne or liquidborne particles, particularly methods for distinguishing biologic and non-biologic particles in real-time, that would also assist in the identification the source of the particles are highly desirable. The real-time detection capability (total particle and microbe counts) is an enabling feature for implementing other real time monitoring devices, such as video camera, in order to have a more comprehensive surveillance and monitoring of area of interest. Such methods would allow for the determination of sources of contamination in controlled environments such as clean rooms, and provide improved methods for the control and prevention of contamination.

SUMMARY OF THE INVENTION

The detection methods and systems of the present invention can be used to detect the presence of particles in an environment and to correlate the detection of the particle with an event in the environment so that the source, or most probably source, of the particles can be identified. Such methods and systems have particular utility for detecting particulate contamination and also in the prevention of contamination in clean environments.

One aspect of the present invention provides a method and system to detect and classify particles in liquids or gases by simultaneously measuring the size and any intrinsic fluorescence from the particles. The method and systems further provide for the real time visual monitoring of an environment of interest and to the identification of probably sources of the particles detected in the environment by the real-time particle detector. Another aspect of the present invention provides methods to differentiate and/or classify biological particles from inert particles. Yet other aspects of the present invention provide methods to identify the source, or most probably, source of biological contamination in clean environments by time correlating real-time particle detection data with image data of the monitored environment. The advantages of this detection scheme and methods over the prior art are several. For one it provides a deterministic particle measurement methodology for characterizing particles rather than relying on statistical models employed in the prior art for particle characterization. The deterministic measurement methodology enables more definitive assignment of particle characteristics than the prior art and less reliance on statistical models. It also reduces the possibility of false positives in microbial detection, for example, pollen (larger sizes than microbes) and smoke particles (smaller sizes than microbes) can be excluded from detection. And, it allows detailed analyses of data collected on each individual particle for characterizing the particle, such as intensity of fluorescence signal from a particle as a function of its cross-sectional area or volume, for the purpose of determining the biological status of the particles, as well as for providing methods to identify in real-time contamination and the sources of contamination resulting in prompt corrective action.

The current invention comprises three main components: (1) a detection system, preferably an optical system, for detecting and measuring individual characteristics of particles, such as particle size and biological properties; (2) an image recoding device and system for recording images of the environment being monitored, e.g., the area in the vicinity of the detector; and (3) a data recording format for assigning particle characteristics, e.g., particle size and fluorescence intensity, to individual particles, optionally computer readable program code for differentiating microbes from non-microbes (e.g. inert dust particles), and a data processing format for time correlating image data to the particle detection data.

BRIEF DESCRIPTION OF THE DRAWINGS

Further features and advantages of the present invention will be seen from the following detailed description, taken in conjunction with the accompanying drawings.

DETAILED DESCRIPTION OF PREFERRED EMBODIMENTS

Figure 1:
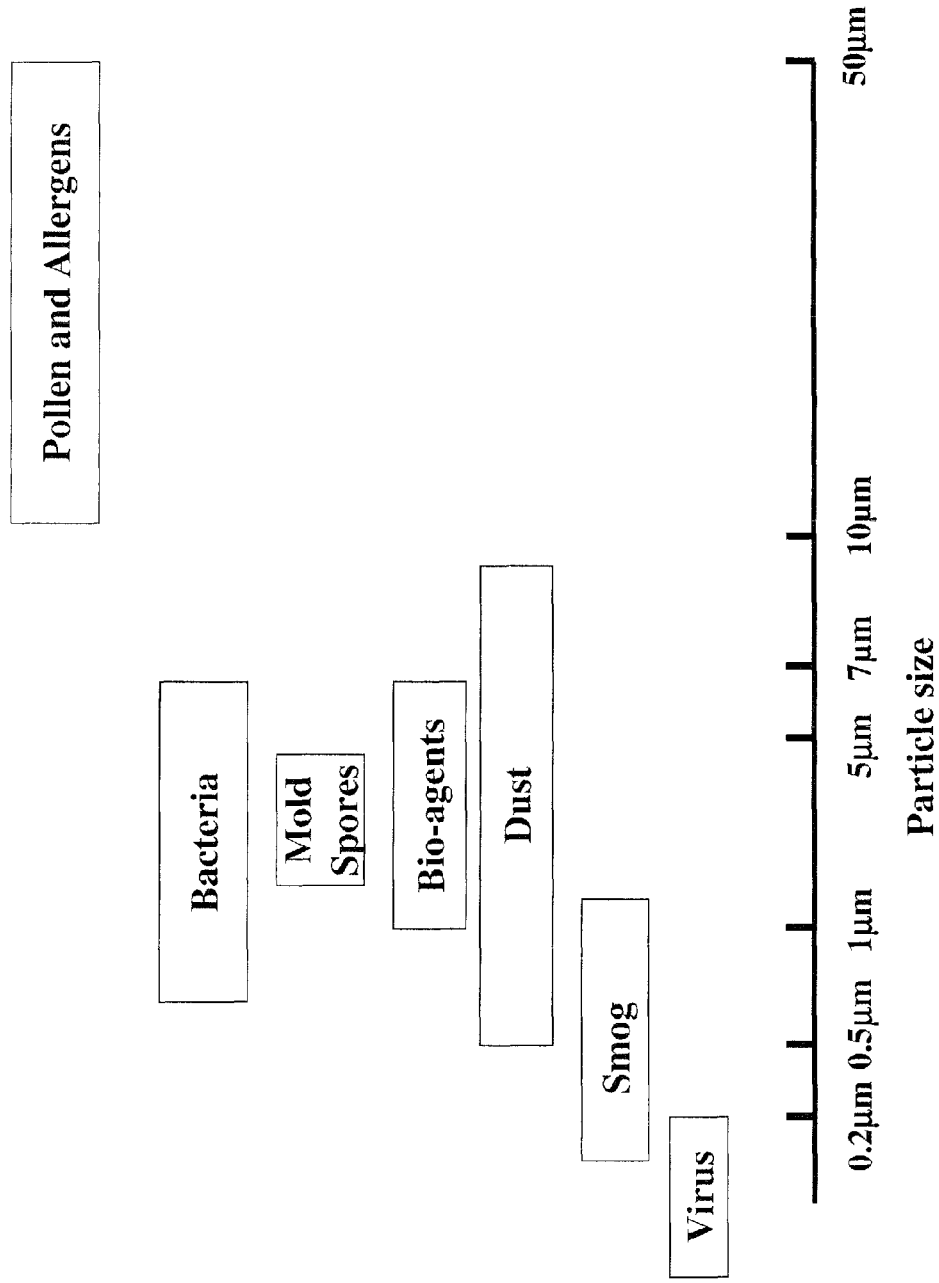
FIG. 1 is a plot showing particle size ranges of several airborne inert and microbial particulates.
Figure 2:
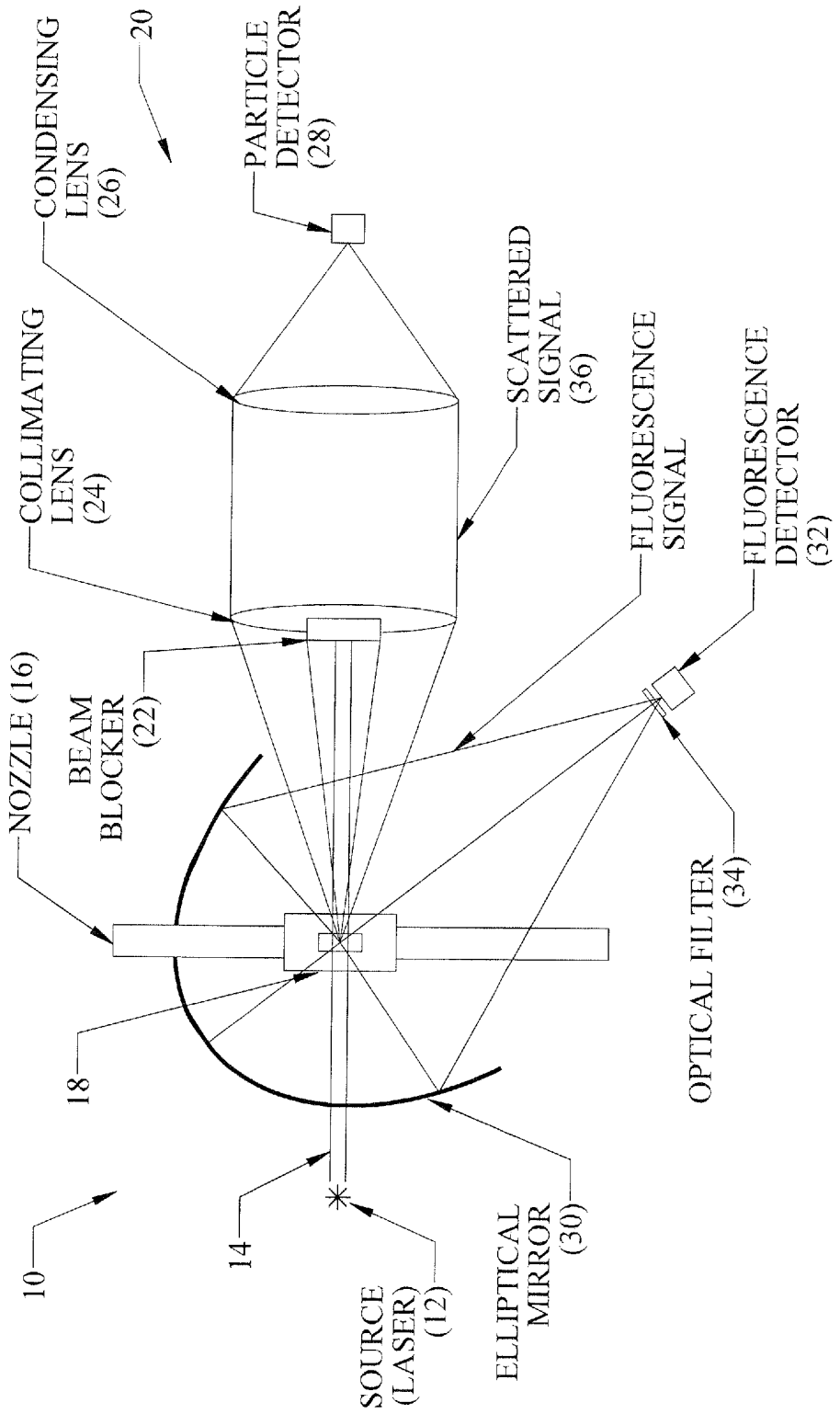
FIG. 2 is a schematic diagram of an optical system for use with the present invention that simultaneously measures particle size and fluorescence of particles in a fluid.

The methods and systems of the present invention can be used to detect the presence of particles in an environment and to correlate the detection of the particle with an event in the environment so that the source, or most probably source, of the particles can be identified. The methods and systems are particularly useful for detecting particulate contamination in controlled environments, determining sources of contamination, and also in the prevention of contamination in such environments.

In one embodiment of the present invention, the methods and systems can be used to detect and identify biologic and non-biologic particles in a controlled environment, and to further provide methods to identify the source of, or most probable source of, any detected biological particles. Such methods and systems are particularly useful for monitoring clean room environments, for example, pharmaceutical clean rooms, for biological contamination and for determining probably contamination sources, for example, identifying a person introducing contamination by entering a controlled environment wearing a dirty gown, so that corrective and/or preventative action can be taken. In one embodiment, methods are provided for the real-time detection particles and the classification of those particles as biologic and non-biologic particles using particle size and fluorescence detection, and an imaging device for the real time monitoring the environment and for further identifying sources of the particles.

The current invention comprises: (1) a detector for detecting particles and optionally measuring characteristics of the particles (e.g., particle size); (2) optionally, a second detector system for measuring pre-determined characteristics of particles (e.g., intrinsic fluorescence); (3) a data recording format for recording and time-stamping the detection of a particle, and optionally for recording and assigning properties to the detected particle, e.g., particle size, intrinsic fluorescence intensity or other properties, and, optionally, computer readable program code for differentiating biologic particles from non-biologic particles (e.g. inert dust particles); (4) an image recording system for monitoring and recording images in the vicinity of the detector or sample intake for the detector and for time-stamping the recorded images; and (5) a data processing system for time correlating the real-time time-stamped particle detection data with the time-stamped visual image data.

In an exemplary embodiment of the invention, the method to detect particles in an environment comprises: providing a detection system for detecting particles; sampling a fluid (e.g., air or a water) from the environment; in real-time using the detector to detect particles in the sample fluid; measuring the particle size of the particles; determining if a detected particle is a biologic or non-biologic particle, for example by simultaneously, or substantially simultaneously, measuring intrinsic fluorescence; time-stamping the particle detection data; providing an image recording system, for example, a digital video camera; using the image recording device to view and record the image seen in the vicinity of the detector or the sample intake of the detector; time-stamping in real time the image data; time correlating the detection of a particle with an image recorded by the image recording system of when the particle was detected; and using the data to determine the source of the particle; and optionally using the data to correct and/or prevent the contamination in the environment. Optionally, the methods of the present invention may also include a alarm system which provides an alarm signal when biologic particles are detected. Such an alarm system may have a pre-determined threshold, above which the alarm signal would be provided.

The term "fluid borne particles" as used herein means both airborne particles and liquid borne particles. Liquid borne particles include those in water or other liquid media. Fluid borne particles also includes those in gases. Waterborne particles include those in water and in liquids comprising water.

The term "biological particle" as used herein refers to any airborne or waterborne particles, pathogen, biological agent, or toxin that could potentially harm or even kill humans exposed to such particles if present in the air or water, or in other liquids or gases, in sufficient quantities.

The term "biological agent" is defined as any microorganism, pathogen, or infectious substance, toxin, biological toxin, or any naturally occurring, bioengineered or synthesized component of any such microorganism, pathogen, or infectious substance, whatever its origin or method of production. Such biological agents include, for example, biological toxins, bacteria, viruses, rickettsiae, spores, fungi, and protozoa, as well as others known in the art.

"Biological toxins" are poisonous substances produced or derived from living plants, animals or microorganisms, but also can be produced or altered by chemical means. A toxin, however, generally develops naturally in a host organism (i.e., saxitoxin is produced by marine algae), but genetically altered and/or synthetically manufactured toxins have been produced in a laboratory environment. Compared with microorganisms, toxins have a relatively simple biochemical composition and are not able to reproduce themselves. In many aspects, they are comparable to chemical agents. Such biological toxins are, for example, botulinum and tetanus toxins, staphylococcal enterotoxin B, tricothocene mycotoxins, ricin, saxitoxin, Shiga and Shiga-like toxins, dendrotoxins, erabutoxin b, as well as other known toxins.

The methods of the present invention can be used with a variety of particulate detection systems. Preferred are optical particle detection systems. Optical detection systems include those that measure particle size and other particle characteristics. Most preferred are optical detection systems that simultaneously can detect and measure particle size and the fluorescence of a particle. While the methods are described with reference to optical systems, the methods of the present invention may also be used with other particle detection devices.

A preferred optical particle detection system of the present invention has two optical sub-assemblies: (a) an optical setup to measure the particle size and (b), simultaneous or substantially simultaneously to the particle size measurement, an optical setup is used to measure the fluorescence level from the particle being interrogated. As an example, the preferred embodiment of the current invention uses the well-known and often used Mie scattering detection scheme to measure particle size, but applies it in a novel way, enabling the system to make highly accurate measurements of airborne particles with size ranges from 0.5 microns to 20 microns. This capability to make fine distinctions in size is important in order to determine the class of microbe, because different classes of microbes have different size ranges as illustrated in FIG. 1. In one preferred embodiment of the current invention an elliptical mirror is positioned to collected fluorescence emission from the same particle as it is being measured for size.

In one embodiment of the present invention, a detection device that simultaneously, or substantially simultaneously, detects and measures particle size and intrinsic florescence from particles, and can further differentiate and/or classify a particle is a biologic or non-biologic particle (e.g., an inert particle) is used. Examples of suitable optical detection systems for simultaneously measuring the particle size and/or fluorescence of particles in fluid media include those described in U.S. patent application Ser. Nos. 11/193,204, 11/457,988, 11/768,103, and 12/268,366, the disclosures of which that are not inconsistent with the disclosure herein are hereby incorporated by reference. In these detection systems light and/or fluorescence scattered or emitted by a particle in a sample fluid is simultaneously detected by a photodiode to determine particle size and by a PMT detector to detect the fluorescence, from which the biologic or non-biologic nature of the particle can be determined. These optical detection devices provide for the real-time detection of particles and the classification of the particles as biologics and non-biologics.

FIG. 2 is a schematic representation 10 of an optical system for a fluid particle detector system according to an exemplary embodiment of the invention. The system is designed, for example to detect fluid borne particles, for example, biologic particles in air or liquid media in industrial applications such as food production, pharmaceutical manufacturing and hospitals, as well as clean room applications, and in other civilian applications, for example, in building or public transportation security, to detect harmful levels of airborne or liquid borne particles that may exist naturally such as mold or bacteria, or which may have been accidentally, inadvertently, naturally or deliberately released. The methods and systems of the present invention also may be used to detect bio-terrorist agents deliberately released by terrorists or others.

As shown in FIG. 2 the system 10 includes an excitation source 12 to provide a beam of electromagnetic radiation 14 having a source wavelength. The excitation source is selected to have a wavelength capable of exciting intrinsic fluorescence from metabolites inside microbes. Examples of suitable excitation sources include UV light and visible radiation sources, such as UV light and visible light lasers, LEDs and the like. By way of example, the excitation source 12 preferably operates at a wavelength in the range of about 270 nm to about 410 nm, preferably about 350 nm to about 410 nm. A wavelength of about 270 nm to about 410 nm is chosen based on the premise that microbes comprise three primary metabolites: tryptophan, which normally fluoresces at excitation wavelengths of about 270 nm with a range of about 220 nm-about 300 nm; nicotinamide adenine dinucleotide (NADH) which normally fluoresces at excitation wavelengths of about 340 nm (range about 320 nm-about 420 nm); and riboflavin which normally fluoresces at excitation wavelengths of about 400 nm (range about 320 nm-about 420 nm). In the case of bacterial endospores, dipicolinic acid (DPA) normally fluoresces at excitation wavelengths of about 400 nm (range about 320 nm-about 420 nm). Preferably, however, the excitation source 12 has a wavelength in the range of about 350 to about 410 nm. This wavelength range ensures excitation of two of the three aforesaid primary metabolites, NADH, and riboflavin in bio-agents, and DPA, but excludes excitation of interferences such as from diesel engine exhaust and other inert particles such as dust or baby powder. In one embodiment, the source 12 has a wavelength of about 405 nm. Thus, in a preferred embodiment the present invention makes a judicial selection of the wavelength of the excitation source 12, which retains the ability of exciting fluorescence from NADH and riboflavin (foregoing the ability to excite tryptophan) while excluding the excitation of interferents such as diesel engine exhaust. This step is taken to reduce false alarms generated by diesel exhaust (which can be excited by short UV wavelengths such as 266 mm light).

In the detection system 10 illustrated in FIG. 2, a fluid sample, e.g., environmental air (or a liquid sample), is drawn into the system through a nozzle 16 for particle sampling. Nozzle 16 has an opening 18 in its middle section (the opening forming a sample cell) to allow the laser beam to pass through the particle stream. The fluid sample cell may be a gas (e.g., air) sample cell or liquid (e.g., water) sample cell. Portions of the excitation source passing through the sample area are scattered at various angles by various sized particles in the sample stream, and unscattered portions of the beam of light remain unscattered passing through the sample area. Directly downstream from the laser beam is a Mie scattering particle-size detector 20. Mie scattering particle-size detector 20 includes a beam blocker 22 in front of collimator lens 24, and a condenser lens 26 for focusing a portion of the light beam 14 scattered by particles in the sample stream onto a particle detector 28.

Off axis from the laser beam 14, an elliptical mirror 30 is placed at the particle-sampling region in such a way that the intersection of the incoming particle stream and the laser beam is at one of the two foci of the ellipsoid, while a fluorescence detector 32 (in this case a photo-multiplier tube (PMT)) occupies the other focus. This design utilizes the fact that a point source of light emanating from one of the two foci of an ellipsoid will be focused onto the other. In this optical design, the elliptical mirror 30 concentrates the fluorescence signal from microbial particles and focuses it onto the fluorescence detector 32. An optical filter 34 is placed in front of the fluorescence detector to block scattered excitation laser light and pass the induced fluorescence. In one embodiment, the optical filter is a high pass filter that blocks scattered light below about 450 nm.

The beam blocking device 22 on the opposite side of the same cell from the radiation source 12 blocks at least a portion of the unscattered excitation source and can also be used for limiting the range of particles measured to a predetermined size range. The beam blocker 22 is designed to absorb, stop and/or contain non-scattered elements of the beam of electromagnetic radiation 14, e.g. the laser beam, and may comprise light absorbent materials, such as vinyl, fluoroelastomers, metallic materials or the like, and/or geometries designed to collect and contain the radiation attached to a front surface of, for example, an optical element. Other features and considerations for the beam blocker 22 are disclosed in some of the earlier US patents to Hamburger et al. listed above, and in PCT Application Serial No. PCT/US2006027638, the disclosures of which that are not inconsistent with the disclosure herein are incorporated herein by reference.

The particle detector 20 may comprise, for example, a photodiode for detecting scattered light for size the particles, for example, as described in the earlier US patent to Hamburger et al., listed above, the disclosure of which that is not inconsistent with the disclosure herein is incorporated herein by reference.

The system of the present invention also further comprise a processing unit for processing particle size distribution data and particle fluorescence data at a given time and displaying this information on an output device. The data may for example be displayed as a histogram. The device and methods of the present invention may further comprise computer readable program code for processing and integrating detected particle size and detected intrinsic fluorescence, and for differentiating between biologic and non-biologic particles. The processing unit also can time-stamp data in real time, providing a time record of when particles are detected. Optionally, the data processing unit can provide alarm signals if the number of biologic particles detected is above a threshold value. Suitable alarm signals include, but are limited to, audio alarms and flashing light alarms.

The present invention's use of Mie scattering also facilitates the placement of optical components for the detection of light induced fluorescence to concurrently examine individual particles for the presence of the metabolites NADH, riboflavin and other bio-molecules (e.g. dipicolic acid), which are necessary intermediates for metabolism of living organisms, and therefore exist in microbes such as bacteria, fungi (e.g. yeasts and molds), and spores. If these chemical compounds exist in a bio-aerosol, they are excited by the photon energy excitation source and subsequently emit autofluorescence light which may be detected by an instrument based on the detection scheme outlined above. While this detection scheme is not capable of identifying the genus or species of microbes, and viruses may be too small and lack the metabolism for detection, this detection scheme's ability to simultaneously, or substantially simultaneously, determine for each particle the size of the particle and if it is biologic or inert indicates to the user the presence or absence of microbial contamination in the environment being sampled.

The methods of the present invention further provide for time correlating the real-time particle detection data with time-stamped image data of the environment sampled by the detector unit. This allows for the detection of particles in the environment to be time-matched to image data of the environment recorded in real-time to show, for example, an event in the environment occurring at or around the time that particles are detected. This is particularly applicable to the detection of particles that are classified as biologics. The ability to quickly correlate in real time the detection of biologic particles in, for example, a pharmaceutical clean room during product production with the event that introduced the contamination allows manufactures to quickly halt production, take corrective action before resuming productions, and may reduce production losses that would occur if using conventional culture growth methods that take days for results to be obtained. This real-time ability to both view time-matched image data and detection data provides for more efficient product release and to decreased production losses when possible contamination is quickly detected.

Figure 3:
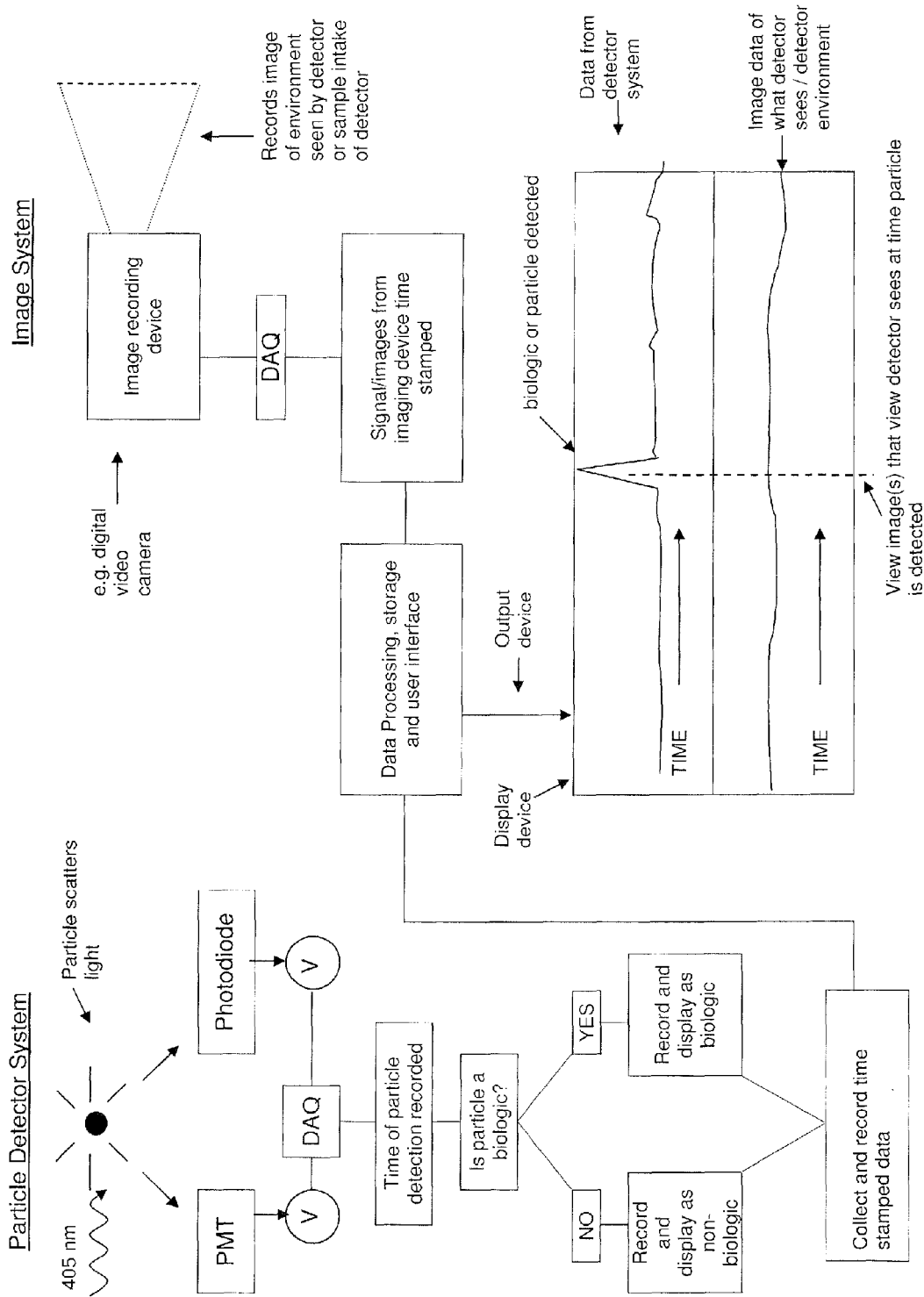
FIG. 3 is a block diagram of a particle detection system and imaging system in accordance with the present invention.

One embodiment of the detection and imaging methods of the present invention is illustrated as a block diagram in FIG. 3. A particle detector system, such as that described above, comprises a 405 nm laser light source which interacts with particles present in the fluid being sampled from the environment under test. Particles in the sample will absorb the light, scatter the light and/or emit fluorescence. The scattered light and fluorescence from particles are detected by a photodiode and PMT (photomultiplier tube) respectfully, as further described above. The voltage signal from these detectors is sent to a data acquisition system (DAQ in FIG. 3). From these signals, the fluorescence power and particle size can be determined, from which information such as the fluorescence cross-section (based on surface area or volume) may also be calculated. Other parameters may also be determined from the data by the data acquisition and processing system. One or more pre-determined thresholds, such as the scatter thresholds (to set upper and lower limits for the size range of particles detected), a fluorescence intensity threshold (sets a fluorescence intensity below which a particle is considered non-fluorescing and hence inert), and a volumetric threshold or fluorescence cross-sectional threshold (sets a threshold above which a particle is recorded as a biologic particle below the threshold it is recorded as an inert particle) can set and used by the data acquisition system to classify detected particles as biologic or non-biologic. Other features and considerations of thresholds are disclosed in U.S. patent application Ser. No. 12/268,366, the disclosure of which that is not inconsistent with the disclosure herein is incorporated herein by reference. As illustrated in FIG. 3, the data acquisition and processing system also time-stamps and records when particles are detected by the detector, and further determines and records the biologic or non-biologic nature of the particles. The data acquisition and processing system also can display in real-time particle detection data on an output device, for example, as a histogram, as well as sound a alarm if the particle count or biological particle count exceeds a threshold. Any suitable data display or output device can be used with the methods of the present invention.

FIG. 3, also shows an imaging device that is preferably mounted in the vicinity of the detector and/or sample inlet. Imaging systems useful with the present invention are any systems that allow for the recordation of images in real-time. Examples of imaging devices include, but are not limited to, digital video cameras, although other imaging devices may also be used. In one embodiment the imaging device is a digital video camera.

The image recording device records images of the environment in the vicinity of the sample inlet of the detector. Preferably, the imaging device is placed to view and record images of the field of view of the detector, and in particular the sample intake of the detector system. Typically, the detector and/or sample inlet is placed adjacent to or very near the area in the environment to be monitored. In some embodiments, the detector unit and sample inlet may be adjacent to each other, i.e., the sample fluid is collected by a sample inlet in the casing of the detector optical unit. In other embodiments, the sample may be collected away from the detector optical unit the sample fluid being transported to sample inlet port of the detector unit by, for example, a tube connected between the sample inlet port and the sampling location. This configuration is useful when the detector is located outside of an isolated (controlled environment space such as a glove box) and sample fluid, i.e. air, is collected from inside of the isolator via a tube and brought to the detector located outside of the isolator. The image recording device is preferably movable so that it can be placed in any suitable location to monitor the environment where sample are being collected and tested by the detector. The field of view of an image recoding device may vary considerably. In some embodiments, the field of view may be in the range of about 5 to 180 degrees. In other embodiments the field view recorded by the imaging recording device may be up to 360 degrees. While FIG. 3 only shows one imaging devices, multiple imaging devices may also be used with the present methods to provide images from more than one location in the environment being monitored. Also, in some embodiments, it may be desirable to place imaging devices away from the detector and sample inlet. In some embodiments, imaging devices may be located throughout the environment where the detector (or detectors) is located.

The imaging device (or devices) records in real-time images of the environment in which the detector is located as particle detection data is being collected. In particular, the imaging device may view the sample intake region of the detector. The data from the imaging device is time-stamped by the data acquisition system. In preferred embodiments, each frame recorded by the imaging device is time and/or date stamped. These frames are preferably recorded as video data files by the data acquisition system.

The data acquisition system for the imaging device may be the same or different from the data acquisition system of the detector. In preferred embodiments, the data acquisition system for the imaging device and particle detector are the same system. The data from the particle detection system and imaging device (e.g., video camera) are processed by a data processing system, which may or may not be the same as the data acquisition systems. The data processing system may comprises one or more selected from data acquisition systems, data collection recording formats, output devices, user interfaces for displaying data, and computer readable code for differentiating microbes from inert particles. One aspect of the data processing system is to correlate in time (time-match) the real-time detected signals from the particle detector system with the images recorded by the imaging system of the environment in sample fluid is collected. The data processing system further stores the data and provides a user interface system, including an output device.

The methods of the present invention provide for data collected by the detector system to be linked in real-time to the image data, thus allowing a user of the system to correlate in time the detection of a particle and to an event in the environment at the time the particle was detected. Thus, when a biologic particle is detected, a user is also able to view a time-stamped image of the environment, for example, with the detector inlet when the particle was detected. A user is thus able to look for and identify probable sources of contamination. For example, a worker entering a clean room wearing a dirty gown or not wearing a protective gown. Methods of the present invention thus provide for the identification of possible contamination sources detected by the particle detector in real time. The data illustrates the advantages of the methods of the present invention for detecting and identifying contamination and its probable source.

The examples provided herein are intended to illustrate certain embodiments of the present invention, but are not to be construed as limiting and do not exemplify the full scope of the invention.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

The invention claimed is:

1. A method for the detection of particles in a fluid and for the identification of the source of the particles comprising:
    drawing a fluid to be sampled through a sample cell;
    illuminating particles in the fluid continuously as the particles pass through the sample cell;
    using a detector system to detect individual particles continuously as the particles pass through the sample cell;
    time-stamping a signal from the detector indicating the presence of particles in the sample cell;
    using one or more image recording devices to record image data of the environment of the detector;
    time-stamping the image data;
    time correlating the time-stamped image data to the time-stamped detector signal to determine the source of contamination; and
    classifying individual particles as biologic or non-biologic particles on the basis of both particle size and fluorescence intensity measured for each individual particle.

2. The method of claim 1, wherein the particles are microbial particles or biological particles.

3. The method of claim 1, further comprising an electronic apparatus to simultaneously collect particle detection system signals and image recording device signals, and an electronic storage device capable of storing the signals with time-stamped information.

4. The method of claim 1, further comprising computer readable program code to correlate time-stamped signals from the particle detection system and image recording device data, and a data display format for showing both signals in time sequence graphics.

5. The method of claim 1, where the method comprises a data recording format that assigns both particle size and fluorescence intensity to an individual particle, and computer readable program code for differentiating from non-microbes, and for correlating time-stamped visual data to the particle detection data.

6. The method of claim 1, further comprising using computer readable program code for correlating/time-stamping particle detection signals and visual image signals.

7. The method of claim 1, further comprising differentiating biological particles from inert particles in a fluid.

8. The method of claim 7, wherein the fluid comprises air or water.

9. The method of claim 1, wherein the image recording device is movable and able to be placed to view to a suitable direction from the particle detection system.

10. A method of detecting particles in a fluid which comprises drawing a fluid to be sampled through a sample cell, illuminating particles in the fluid continuously as the particles pass through the sample cell, simultaneously measuring particle size of the particle and detecting intrinsic fluorescence from the particle continuously as the particle passes through the sample cell, visually recording the environment in which detection occurs to determine sources of contamination, and classifying individual particles as biologic or non-biologic particles.

11. A method for detection of biologic and non-biologic particles in a fluid comprising:
  drawing a fluid to be sampled through a sample cell;
  illuminating particles in the fluid continuously as the particles pass through the sample cell;
  measuring particle size and fluorescence from particles in the fluid continuously as the particles pass through the sample cell;
  determining if particles are biologic or non-biologic from the particle size and fluorescence data;
  classifying individual particles as biologic or non-biologic particles;
  assigning a time-stamp to data regarding the presence of biologic and non-biologic particles passing through the sample cell;
  recording image data of the environment in the vicinity of the detector;
  time-stamping the image data;
  time correlating the data regarding the presence of biologic and non-biologic particles passing through the sample cell and image data.

12. The method of claim 11, further comprising sounding an alarm when biologic particles are detected.

13. The method of claim 1, wherein using one or more image recording devices to record a image of the environment of the detector comprises using one or more image recording devices to record an image of the environment in the vicinity of a sample inlet of the detector.

14. The method of claim 13, wherein using one or more image recording devices to record an image of the environment in the vicinity of a sample inlet of the detector includes using one or more image recording devices to view the sample intake region of the detector.

15. The method of claim 13, wherein the vicinity of a sample inlet of the detector includes a clean room.

* * * * *